United States Patent
Andresen et al.

(10) Patent No.: US 8,545,466 B2
(45) Date of Patent: Oct. 1, 2013

(54) DEVICE FOR TREATMENT OF WOUNDS WITH REDUCED PRESSURE

(75) Inventors: Angelica Andresen, Torslanda (SE); Ulf Johannison, Landvetter (SE)

(73) Assignee: Mölnlycke Health Care AB, Göteborg (SE)

( * ) Notice: Subject to any disclaimer, the term of this patent is extended or adjusted under 35 U.S.C. 154(b) by 742 days.

(21) Appl. No.: 12/666,002

(22) PCT Filed: Jun. 24, 2008

(86) PCT No.: PCT/SE2008/050749
§ 371 (c)(1),
(2), (4) Date: Dec. 22, 2009

(87) PCT Pub. No.: WO2009/002260
PCT Pub. Date: Dec. 31, 2008

(65) Prior Publication Data
US 2010/0324510 A1 Dec. 23, 2010

(30) Foreign Application Priority Data
Jun. 27, 2007 (SE) ........................................ 0701546

(51) Int. Cl.
*A61M 27/00* (2006.01)
(52) U.S. Cl.
USPC .......................................... 604/319; 604/543
(58) Field of Classification Search
CPC ........................................................ A61M 27/00
USPC ................. 604/540, 541, 543, 313, 317–327
See application file for complete search history.

(56) References Cited

U.S. PATENT DOCUMENTS

| 3,572,340 A | 3/1971 | Lloyd et al. |
| 3,742,952 A | 7/1973 | Magers et al. |
| 4,382,441 A | 5/1983 | Svedman |
| 4,525,166 A | 6/1985 | Leclerc |
| 4,969,880 A | 11/1990 | Zamierowski |
| 5,340,363 A * | 8/1994 | Fabo .............................. 604/304 |
| 5,385,494 A | 1/1995 | Wilhelmi |

(Continued)

FOREIGN PATENT DOCUMENTS

| GB | 2228682 A | 9/1990 |
| WO | WO 97/42985 | 11/1997 |

(Continued)

OTHER PUBLICATIONS

International Search Report, corresponding to PCT/SE2008/050749, mailed Sep. 29, 2008.

(Continued)

*Primary Examiner* — Philip R Wiest
*Assistant Examiner* — Benjamin Klein
(74) *Attorney, Agent, or Firm* — Ballard Spahr LLP

(57) ABSTRACT

Device for treating wounds with reduced pressure. The device comprises a sealing film, which is placed sealingly around the wound to cover the latter, an underpressure source, as well as a tube, which connects a space over the wound and beneath the sealing film to the underpressure source. The interior of the tube comprises a longitudinal first strand made of a hydrophobic material, as well as a second strand, made of an open-pored hydrophilic material, extending longitudinally over at least a part of the length of the tube. The said material strands are enclosed in a tube casing made of a flexible material.

31 Claims, 9 Drawing Sheets

(56) References Cited

U.S. PATENT DOCUMENTS

| | | | |
|---|---|---|---|
| 5,636,643 | A | 6/1997 | Argenta et al. |
| 5,645,081 | A | 7/1997 | Argenta et al. |
| 6,071,267 | A * | 6/2000 | Zamierowski ............... 604/289 |
| 6,613,955 | B1 * | 9/2003 | Lindsay et al. ............... 604/378 |
| 6,855,135 | B2 | 2/2005 | Lockwood et al. |
| 7,517,536 | B2 * | 4/2009 | Ko ............................... 424/443 |
| 2002/0193030 | A1 * | 12/2002 | Yao et al. ...................... 442/366 |
| 2008/0082059 | A1 * | 4/2008 | Fink et al. ..................... 604/305 |
| 2008/0200906 | A1 * | 8/2008 | Sanders et al. ............... 604/543 |
| 2008/0294147 | A1 * | 11/2008 | Radl et al. .................... 604/543 |
| 2011/0046584 | A1 * | 2/2011 | Haggstrom et al. .......... 604/319 |

FOREIGN PATENT DOCUMENTS

| | | |
|---|---|---|
| WO | WO 2006/025848 A2 | 3/2006 |
| WO | WO 2006/075950 | 7/2006 |
| WO | WO 2006/114638 A2 | 11/2006 |

OTHER PUBLICATIONS

Written Opinion, corresponding to PCT/SE2008/050749, mailed Sep. 29, 2008.

Mark E. Chariker, M.D., Katherine F. Jeter, E.D. ET Tess E. Tintle, BSN ET, John E. Bottsford, Jr., M.D., Contemporary Surgery, Issue 34, Jun. 1989, Effective Management of Incisional and Cutaneous Fistulae With Closed Suction Wound Drainage.

B.M. Kostiuchenok, I. I. Kolker, V.A. Karlov, S. N. Ignatenko, L.I. Muzykant, T. D. Samykina, from The Kremlin Papers, The Vacuum Effect in the Surgical Treatment of Purulent Wounds, Sep. 1986, pp. 18-21.

Prof. Yu. A. Davydov, Assistant Professor E. V. Malafeeva, A.P. Smirnov, Candidate of Medical Science V. B. Flegontov Department of General Surgery (Prof. Yu. A. Davydov, Head), Yaroslavl Medical Institute, from the Kremlin Papers, Vacuum Therapy in the Treatment of Purulent Lactation Mastitis, Sep. 1986, pp. 66-70.

Y.N. Usupov and M.V. Yepifanov, Department of Clinical Surgery (Prof. M. I. Lytkin, Head) and Department of General Surgery (Prof. I. G. Peregudov, Head) S. MN. Kirov Military Medical Academy, Leningrad, The Kremlin Papers, Active Wound Drainage Russian Journal: Vestnik Khirurgii, Apr. 1987 (p. 42-45).

Yuu A. Davydov, A. B. Larichev, K. G. Menkov Deparatment of General Surgery (Prof. Yu. A. Dadydov, Head), Yaroslavl Medical Institute, The Kremlin Papers, The Bacteriological and Cytological Assessment of Vacuum Therapy of Purulent Wounds, Oct. 1988, pp. 48-52.

Prof. Yuu. A. Davydov, Candidate of Medical Science A. B. Larichev, A. Yu. Abramov, K. G. Menkov Department of General Surgery (Prof. Yu. A. Davydov, Head), Yaroslavl Medical Institute, The Kremlin Papers, Concepts for Clinical Biological Management of the Wound Process in the Treatment of Purulent Wounds Using Vacuum Therapy, Feb. 1991, pp. 132-135.

International Preliminary Report on Patentability issued on Jan. 5, 2010 for Int'l. App. No. PCT/SE2008/050749, filed on Jun. 24, 2008 (Inventor—Andresen et al.; Applicant—Molnlycke Health Care AB; pp. 1-5).

Extended European Search Report issued on Mar. 14, 2012 for EP Pat. App. No. 08767215.0, national phase of Int'l. App. No. PCT/SE2008/050749, filed on Jun. 24, 2008 (Inventor—Andresen et al.; Applicant—Molnlycke Health Care AB; pp. 1-4).

* cited by examiner

DEVICE FOR TREATMENT OF WOUNDS WITH REDUCED PRESSURE

CROSS-REFERENCE TO RELATED APPLICATIONS

The present application is a national stage application of International Application No. PCT/SE2008/050749, filed Jun. 24, 2008, which International Application claims priority to Swedish Application No. 0701546-4, filed Jun. 27, 2007, which applications are incorporated herein fully by this reference.

TECHNICAL FIELD

The present invention relates to a device for treating wounds with reduced pressure, which device comprises a sealing film, which is intended to be placed sealingly around the wound and cover the latter, an underpressure source, as well as a tube, which is arranged to connect a space over the wound and beneath the sealing film to the underpressure source.

BACKGROUND ART

A number of methods for treating slow-healing wounds, such as infected wounds, diabetes sores, pressure sores or deep wounds, are previously known.

Drainage of, for example, surgical wounds or other weeping wounds with underpressure is a standard treatment which has been used for decades. An example of a manual suction pump for this purpose is described in U.S. Pat. No. 3,742,952.

U.S. Pat. No. 3,572,340 describes a pump in the form of an elastically compressible body made of an open-celled foam material, preferably a polyurethane foam, which body also serves as a receptacle for fluid drained from the wound. The pump is said to have a capacity to maintain an underpressure of 15-80 mmHg for more than 48 hours. A perforated drain is intended to be placed in the wound pocket and is connected to the pump by a tube. A similar device is described in U.S. Pat. No. 4,525,166, in the description of which it is specifically stated that the underpressure not only drains wound fluid but also draws together the wound edges and stimulates tissue growth and healing of the wound. The two latter publications therefore state that vacuum treatment of wounds stimulates wound healing.

The terms vacuum treatment, treatment with reduced pressure and treatment under negative pressure are used interchangeably in the literature. It should be pointed out that, where these terms are used within this description, treatment at a pressure below normal atmospheric pressure is always meant.

Deep wounds have also been treated with a combination of a rinsing fluid supply and subsequent aspiration. Examples of such devices are described in U.S. Pat. No. 5,385,494 and U.S. Pat. No. 4,382,441.

Extensive studies of the effect of both continuous and intermittent treatment of wounds under negative pressure, i.e. pressure below normal atmospheric pressure, were conducted during the 80's in Russian institutions. It was here demonstrated that slow-healing wounds heal substantially faster with the aid of vacuum treatment compared with conventional treatment methods. It was also shown, inter alia, that treatment with reduced pressure produced a significant antibacterial effect. The said Russian studies are described in articles in the Russian medical journal Vestnik Khirurgii. The articles from the said journal are:

1) Kostiuchenok et al, September 1986, pages 18-21.
2) Davydov et al, September 1986, pages 66-70.
3) Usupov et al, April 1987, pages 42-45.
4) Davydov et al, October 1988, pages 48-52.
5) Davydov et al, February 1991, pages 132-135.

In an article by Chariker et al in the journal Contemporary Surgery, issue 34, June 1989, it is stated that vacuum treatment improves the growth of granulation tissue and the wound contraction of wounds which with conventional treatment are very slow-healing.

The vacuum treatment of wounds is also described in U.S. Pat. No. 4,969,880, U.S. Pat. No. 5,645,081 and U.S. Pat. No. 5,636,643.

As examples of applications describing the vacuum treatment of wounds can be cited U.S. Pat. No. 6,855,135 B2 and WO 2006/025848 A2.

Previously known devices for the vacuum treatment of wounds are not satisfactory in all respects. A fundamental problem is that they are quite bulky right in front of the wound, which can result in the wound being able to be subjected by the bulky parts right in front of it to undesirable load stresses, which can be painful for the patient and can disturb the wound healing process. A very major problem is the relatively rigid tubes which connect the wound pocket to the pressure source. The tubes are unwieldy and bulky and can give rise to chafes and, in unfavourable cases, can also cause pressure sores on the patient. Depending on where the patient has the wound, it is often not possible to place the pressure source or an intermediate fluid-receiving receptacle close to the wound, but instead it may be necessary to use relatively long tubes, for example from the foot of the patient right up to the waist, which can cause chafes on patients who are lying or sitting. A further problem with conventional tubes is that it is difficult to achieve satisfactory leak-tightness at the connection between the tube and the sealing film placed over the wound.

If the underpressure for some reason abates, in previously known devices there is a risk of exudate which has previously been aspirated from the wound pocket being transported back and contaminating this, unless a check valve is present at the connection between the tube and the wound pocket.

DISCLOSURE OF INVENTION

As a result of the present invention, the abovementioned problems have been eliminated.

The device according to the invention is characterized in that the interior of the tube comprises at least one longitudinal first strand made of a hydrophobic, soft and elastic material, in that the interior of the tube over at least a part of its length has at least one longitudinal second strand made of a hydrophilic, soft and elastic material, and in that the said material strands are enclosed in a tube casing made of a flexible material.

A tube of this kind is very soft and comfortable for the user and can be configured essentially arbitrarily. A fundamental advantage compared with conventional tubes is that the tube according to the invention does not let sucked-up fluid back to the wound pocket should the underpressure in the system for some reason cease. In such cases, sucked-up fluid is absorbed by the hydrophilic strand in the tube.

According to one illustrative embodiment, the invention is characterized in that the first material strand is constituted by a hydrophobic, open-pored foam material, and in that the second material strand is constituted by a hydrophilic, open-pored foam material.

According to one illustrative embodiment, the invention is further characterized in that the said first and second strands are placed one over the other and have a rectangular cross section.

According to one embodiment, the invention is characterized in that the underpressure source is intended to also serve as a fluid-receiving element for fluid aspirated from the wound and, for this purpose, comprises an elastically resilient, open-pored foam material, as well as a one-way valve, which is arranged to allow an outflow of air from the said element when this is compressed.

According to one embodiment, the invention is here characterized in that the said fluid-receiving element is constituted by a folded or rolled-up portion of the tube.

According to one embodiment, the invention is characterized in that the tube and/or the fluid-receiving element contain(s) a super-absorbent material.

One embodiment of the invention is characterized in that one end portion of the tube casing is provided with a fixing member for fastening the said tube end onto the outer side of the sealing film right in front of a hole made therein, which hole, when the device is used, is placed above the said space over the wound, and in that the said end portion has an opening for connection to the hole.

One embodiment of the invention is characterized in that the said fixing member comprises a tab made of a plastics film, which tab is provided with a peripherally placed fixing means, intended for sealing connection to the outer side of the sealing film around the said made hole.

According to one embodiment, the invention is characterized in that the device comprises a hydrophobic, porous material piece, such as a hydrophobic, open-pored foam material, which material piece is intended to be configured in the shape of the wound and to be placed in the wound beneath the sealing film.

According to one embodiment, the invention is here characterized in that active carbon is placed in the said porous material piece.

According to one embodiment comprising the said hydrophobic, porous material piece, the invention is characterized in that the device comprises an absorption body made of a hydrophilic, porous material, such as a hydrophilic, open-pored foam material, which absorption body is intended to be configured in the shape of the wound and to be placed in this between the sealing film and the said hydrophobic, porous material piece. This absorption body serves as an extra absorption reserve and can take care of a large quantity of exudate should the underpressure for some reason cease.

According to a somewhat modified embodiment comprising the said hydrophobic, porous material piece, the invention is characterized in that the device comprises an absorption pad made of a hydrophilic, porous material, such as a hydrophilic, open-pored foam material, which absorption pad is intended to be placed over the made hole in the sealing film between this and the said plastics tab.

According to one embodiment, the invention is characterized in that the device incorporates an electric pump.

According to one embodiment, the invention is characterized in that the said pump is constituted by a battery-powered piezoelectric pump.

According to one embodiment, the invention is characterized in that the said pump is arranged for detachable connection to the said fluid-absorbing element.

According to a further illustrative embodiment, the invention is characterized in that the device incorporates a manual pump.

According to one embodiment, the invention is here characterized in that the said manual pump is arranged for detachable connection to the said fluid-receiving element.

According to another embodiment, the invention is characterized in that the device incorporates a separate opening diaphragm, which is provided with fixing means for fastening onto the outer side of the sealing film and which is intended to be fixed to the sealing film over the wound, in that the opening diaphragm is configured by a material penetrable with a cannula, which material is self-sealing following removal of the cannula, whereby rinsing fluid and/or wound-healing stimulant can be added via the said opening diaphragm.

According to a further embodiment, the invention is characterized in that the device comprises a thin, hydrophobic sheet of, for example, non-woven fabric, plastic or a foam material, provided with a central opening, which sheet is intended to be placed over and around the wound beneath the sealing film, and in that the thin sheet is soft and flexible and is intended to be pressed by the atmospheric pressure into sealing contact with the skin of the patient around the wound.

According to one embodiment, the invention is characterized in that the interior of the tube has at least one diaphragm valve, which is arranged to only allow a flow in the direction away from the wound towards the underpressure source. Additional security against leakage back to the wound pocket is thereby achieved.

According to one embodiment, the invention is characterized in that the said hydrophobic, porous material piece, on its side which is placed against the wound surface during use, is coated with a perforated coating of an elastic, hydrophobic gel, such as a silicone gel.

According to a somewhat modified embodiment, the invention is characterized in that the device incorporates an elastic mesh, which is coated with a soft, elastic hydrophobic gel, such as a silicone gel, and in that the mesh is intended to be cut to the size of the wound and to be placed next to the wound surface.

According to one embodiment, the invention is characterized in that sealing film and tube are formed into an integrated prefabricated unit.

According to one embodiment, active carbon is placed in the tube.

According to another embodiment, active carbon is placed in the fluid-receiving element.

According to one embodiment, the said tube is connected to the underpressure source by a silicone tube.

BRIEF DESCRIPTION OF DRAWINGS

The invention will be described in greater detail below with reference to the appended drawings, in which.

MODE(S) FOR CARRYING OUT THE INVENTION

Figure 1:
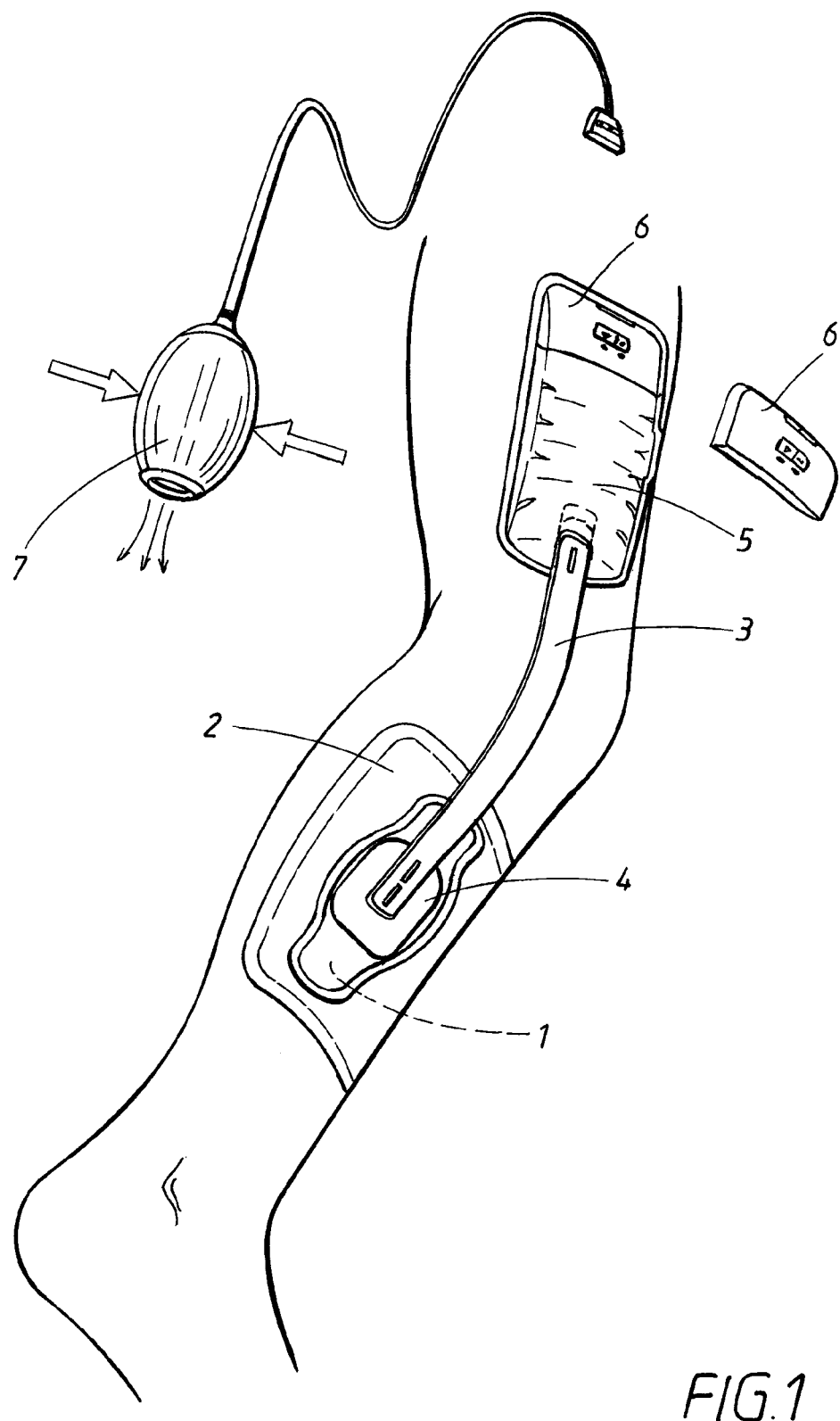
FIG. 1 shows an illustrative embodiment of the device according to the invention.

In FIG. 1, the patient has a wound on the calf. The device according to FIG. 1 comprises a hydrophobic, porous material piece 1, such as a hydrophobic, open-pored foam material. The material piece is cut to the shape of the wound to fill the wound pocket. A sealing film 2 is placed sealingly over the wound and is fixed to the skin of the user.

A tube 3 having a fixing member 4, which latter is fixed to the outer side of the sealing film over a hole made therein, connects the space in the wound pocket to an underpressure source 5. This is also intended to serve as a fluid-receiving element for fluid aspirated from the wound. The underpressure source is of elastically compressible configuration. Upon manual compression, air is squeezed out through a discharge valve (not shown), in the form of a one-way valve, to the environment. A further one-way valve (not shown) is fitted in the tube 3 or in the transition from the tube to the underpressure source. A suitable alternative is to dispose a one-way valve in the tube next to the wound. This prevents an exudate fluid column in the tube from possibly being sucked back to the wound. In this alternative, it may be expedient to additionally fit a non-return valve at the connection of the tube to the fluid-receiving element. An exchange of just the tube or just the fluid-receiving element is thereby enabled. This element can be constituted by a conventional bag of the kind used to collect body fluid.

The said one-way valve and the said non-return valve allow only a flow from the wound pocket to the underpressure source.

Following compression of the underpressure source, this is allowed to expand, whereby an underpressure is created in the underpressure source and the wound pocket. The device according to the invention is intended to be applied to slow-healing wounds. Treatment of the wound can be realized with continuous or intermittent underpressure.

The treatment time is dependent on the condition of the wound and the healing process during the treatment. In the illustrative embodiment shown in FIG. 1, an electric pump is also included, which is provided to supplement the underpressure source and to maintain a predetermined underpressure level in the wound pocket. According to one embodiment, the pump can be constituted by a battery-powered piezoelectric pump 6.

Alternatively, a pumping effect can be achieved by means of wall suction, which is permanently fitted in hospital.

An example of a manual pump is Bellovac® from Astra Tech.

According to an alternative embodiment, the underpressure in the underpressure source 5 and the wound pocket is created entirely by the electric pump 6.

The electric pump 6 is detachably connected to the underpressure source, as is shown in FIG. 1.

According to one expedient embodiment, the underpressure source 5, the tube 3, the material piece 1 filling the wound pocket, and the sealing film 2 are constituted by disposable material, which is discarded in connection with the dressing of the wound.

The device shown in FIG. 1 can be supplemented by a manual pump 7, which can be used as a supplement to the electric pump. After the device has been fitted to the patient, the manual pump is expediently first used to quickly create an underpressure in the underpressure source and the wound pocket, after which the manual pump is disconnected and replaced with the electric pump.

Figure 2:
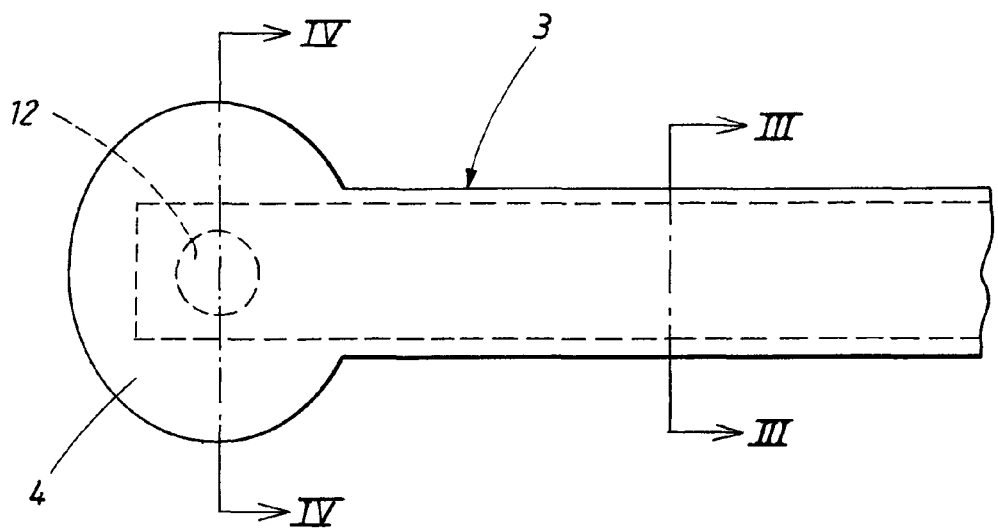
FIG. 2 shows a side view of a first illustrative embodiment of a tube forming part of the device according to the invention.
Figure 3:
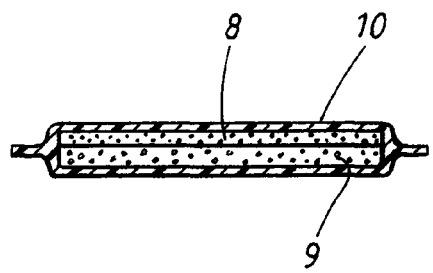
FIG. 3 shows a section along the line III-III in FIG. 2.
Figure 4:
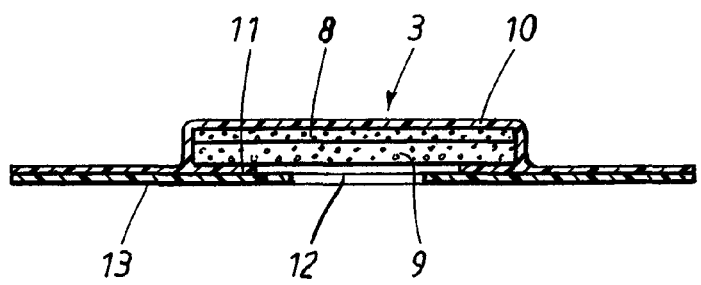
FIG. 4 shows a section along the line IV-IV in FIG. 2.

In FIGS. 2-4, a first illustrative embodiment of a tube is shown in greater detail. The interior of the tube consists of a first strand 8 made of a hydrophobic, open-pored foam material and a second strand 9 made of a hydrophilic, open-pored foam material. In the shown illustrative embodiment, the tube casing consists of two plastics films made of a soft elastic plastic, which plastics films, as is shown in FIG. 3, are connected along the edges of the tube to form a casing which runs around the strands 8 and 9 and is denoted in its entirety by 10. At one end of the tube, the plastics films have a widened portion for the formation of the fixing member 4. The one plastics tab 11 of the widened portion has a central opening 12, which, when the tube is used, is intended to be placed right in front of the made hole in the sealing film. The underside of the plastics tab is provided with a bonding agent 13 for connection to the outer side of the sealing film around the hole made therein. The said bonding agent is expediently constituted by a silicone adhesive, which gives good sealing and prevents leakage at the fixing member. One advantage with silicone adhesive is that the fixing member can be easily detached and refastened to the sealing film should the fixing member end up wrong on the sealing film.

Alternatively, other pressure-sensitive adhesives, such as acrylate, may be used.

A tube of the described kind is soft and pliable and can be of thin configuration. The soft tube is comfortable for the patient and does not give rise to chafes against the skin of the patient when load stresses arise.

The tube can possibly be enclosed in a stocking-like casing, for example for increased strength and/or increased comfort.

The tube and possibly also the collecting receptacle can be provided with a bonding agent, such as silicone, on its outer side, for fastening the tube and the collecting receptacle to the skin of the user. Other types of fixing members, such as suction bodies or the like, are, of course, conceivable.

It is essential that the tube contains both a hydrophobic strand and a hydrophilic strand. The hydrophobic strand 8 is intended to rapidly be able to transport fluid from the wound pocket to a receptacle 5 for collecting fluid discharged from the wound. The hydrophilic strand 9 is intended to absorb fluid. This is especially important should the underpressure for some reason cease. The hydrophilic strand absorbs fluid in the tube and prevents this from being transported back to the wound pocket and contaminating this. In the compressed state, i.e. under negative pressure, the hydrophilic strand should have an absorbency of at least about 5 g/g, whilst at atmospheric pressure it should have an absorbency of at least about 20 g/g.

By the term hydrophobic is here not necessarily meant that the contact angle for the hydrophobic strand must be at least 90°, i.e. that the boundary for hydrophobic and hydrophilic is at this contact angle magnitude. What is essential is that wound fluid can be easily transported in the hydrophobic strand and that the hydrophilic strand has the capacity to suck fluid from the hydrophobic strand.

An example of a suitable hydrophilic foam material for use as the said second strand in the tube is PUR foam having a pore size of a diameter measurement between 0.10 and 1.25 mm, such as between 0.25 and 0.75 mm, for example around 0.50 mm. Polyurethane foam of this kind is, for example, Hypol® from Hampshire Chemical Corporation, Lexington, Mass., USA.

Other absorbent foam materials, such as viscose foam, EVA foam, hydrophilized silicone foam, etc. are also usable as hydrophilic foam material in the tube.

An example of a hydrophobic foam material for use as the said first strand in the tube is hydrophobic PUR foam, for example from Recitel, having a pore size of a diameter measurement between 0.10 and 2.00 mm, such as between 0.50 and 1.25 mm, for example around 1.0 mm. Furthermore, the hydrophobic foam material can be constituted by a foam, which is initially hydrophilic and which is steeped in a hydrophobic component, such as silicone, which gives the foam material hydrophobic characteristics.

The sealing film 2 is constituted by a thin, soft and flexible plastics film, which is coated with bonding agent 14, expediently of silicone, for anchoring the film to the skin of the user around the wound. Suitable characteristics for a silicone adhesive for achieving good sealing characteristics against leakage between skin and plastics film are described in WO 2006/075950. An example of a suitable silicone adhesive is #SR45554 from Wacker.

Figure 5:
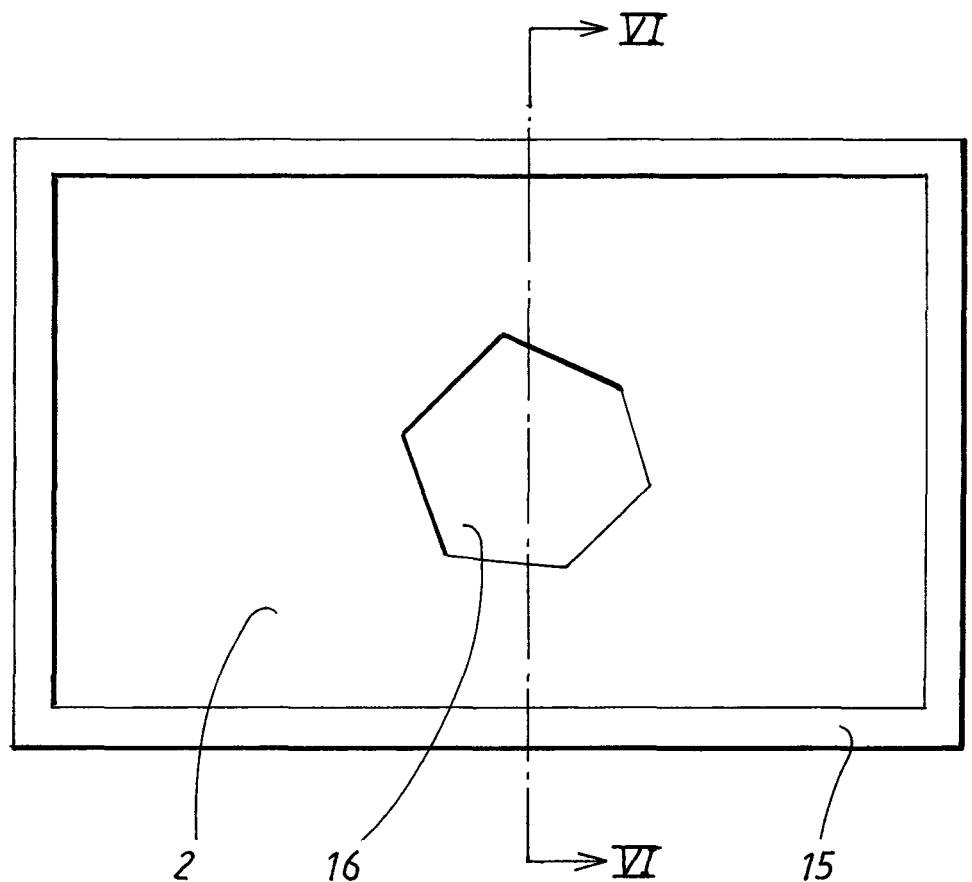
FIG. 5 shows an illustrative embodiment of a sealing film forming part the device according to the invention, in top view.

The film, in order to facilitate handling thereof, is provided with a stiffening edge 15, which is torn off in connection with fastening of the sealing film around the wound. In FIG. 5 there is shown a hole 16 made in the film, which hole, when the film is used, is arranged over the wound, for example centrally over it. The hole does not necessarily need to be directly over the wound. It is sufficient for the wound to be partially overlapped by the hole in order for exudate from the wound to be sucked away.

In the embodiment according to FIGS. 7-10, the components corresponding to similar parts in the embodiment according to FIGS. 2-4 have been provided with the same reference symbols. In the fixing member 4, both the hydrophobic coating and the hydrophilic coating have a widened oval portion 8' and 9' respectively. The elongated part of the tube is provided at its free end with a discharge valve (not shown). The hydrophobic and hydrophilic foam materials in the tube, both in the widened portion and in the elongated portion, are of compressible and elastically resilient configuration. In the illustrative embodiment which is shown here, the tube is intended to serve as a tube and fluid-receiving receptacle, and also as a pump for the generation of underpressure.

In the fixing member, the casing comprises a flexible, soft plastics film 11', which, as can be seen from FIGS. 7-10, has a greater extent than the foam material. The plastics film is coated on the underside with a bonding agent 13', expediently of silicone, such as the abovementioned bonding agent from Wacker. The plastics film is provided with a central opening 12, around which also a number of perforations 12' are provided. The perforations are arranged to allow fluid to flow from the made hole 16 in the underlying sealing film 2 should the opening in the fixing member mistakenly end up right in front of the made hole 16. As a result of the action of the underpressure in the tube, the perforations 12' also cause the plastics film to be sucked in sealing arrangement tightly against the underlying sealing film 2.

The illustrative embodiment shown in FIGS. 7-10 is very flexible with respect to its use. It can be used in combination with a separate sealing film of the kind shown in FIG. 5 and also in combination with an electric pump. Alternatively, the plastics film 11' can serve as the sealing film and the device according to FIGS. 7-10 can serve as a complete unit for underpressure treatment of small slow-healing and seeping wounds, possibly in combination with a material piece made of a hydrophobic foam material, which is placed in the wound pocket. The device according to FIGS. 7-10 can also incorporate a battery-powered electric pump of the kind described above. Alternatively, a manual bellows pump or underpressure from a wall suction device can be used.

Figure 8:
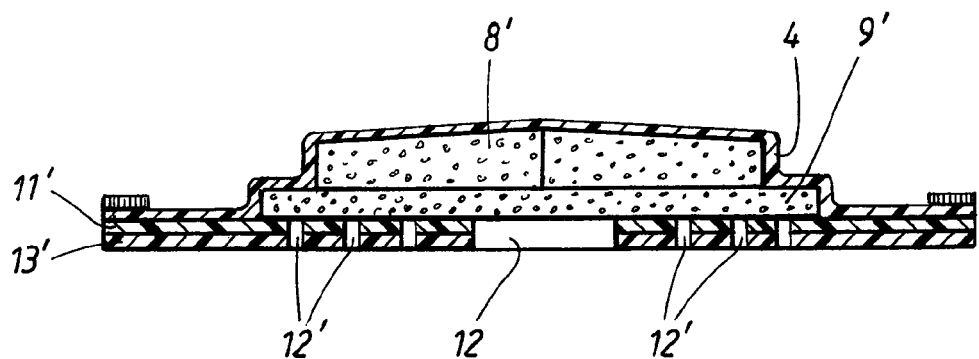
FIG. 8 shows a section along the line VIII-VIII in FIG. 7.
Figure 9:
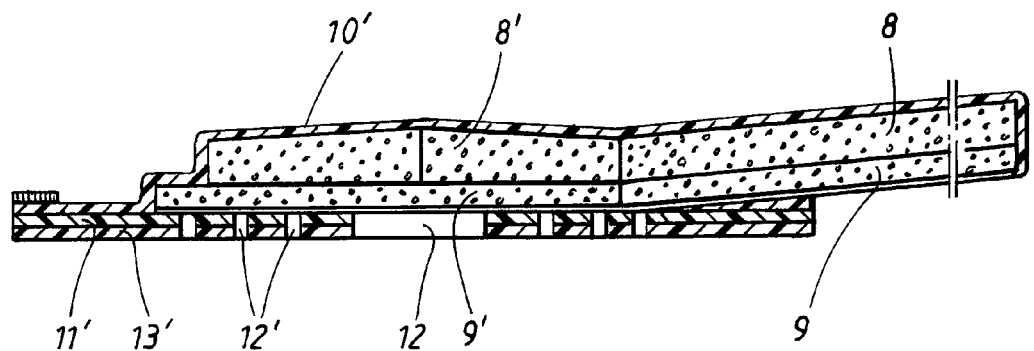
FIG. 9 shows a section along the line IX-IX in FIG. 7.
Figure 10:
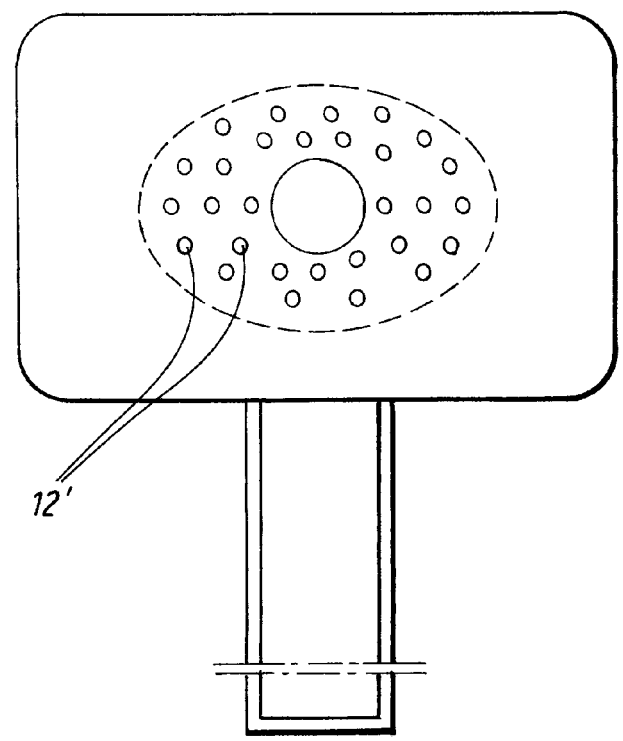
FIG. 10 shows the tube according to FIG. 7 in bottom view.

As can be seen from FIGS. 8 and 9, the hydrophilic coating 9' in the widened portion of the tube is situated next to the opening 12. One advantage with this is that exudate which has been absorbed in the hydrophilic material is retained in this should the underpressure for some reason cease, and contamination of the wound pocket with previously aspirated fluid is thereby prevented. The hydrophilic coating next to the opening serves essentially as a one-way valve. Fluid can flow in through this and onward to the hydrophobic coating when there is underpressure in the tube. By contrast, fluid in the hydrophilic coating will not be sucked back to a hydrophobic foam material in the wound pocket.

Figure 11:
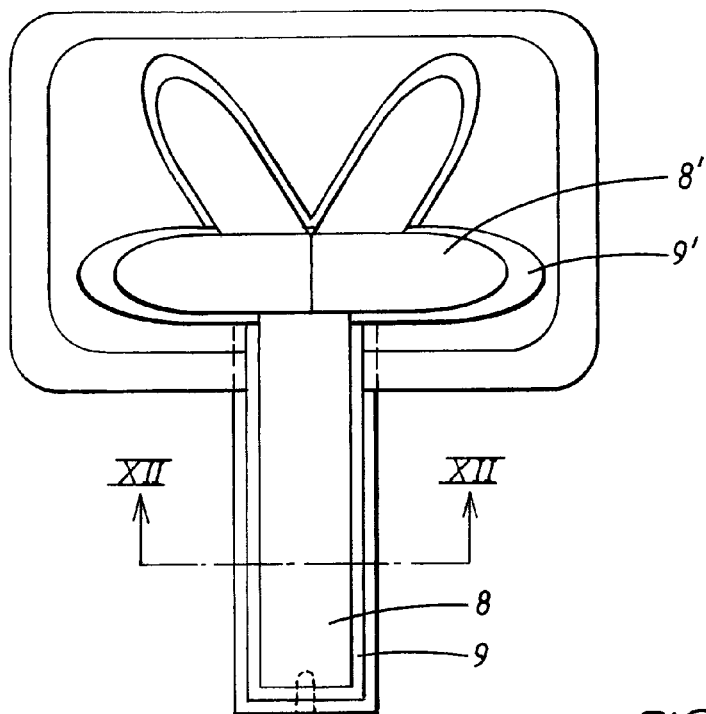
FIG. 11 shows in top view a third embodiment of a tube forming part of the device according to the invention, with associated fixing member.
Figure 12:
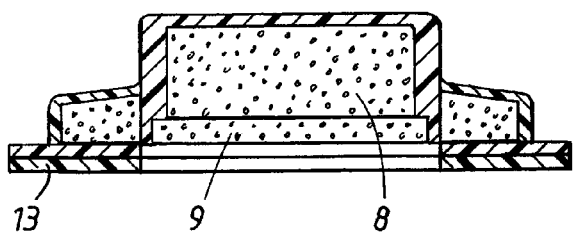
FIG. 12 shows a section along the line XII-XII in FIG. 11.

The embodiment shown in FIGS. 11 and 12 functions in every respect essentially like the embodiment according to FIGS. 7-10 and the working is not therefore described in detail. In the embodiment according to FIGS. 11 and 12, the components corresponding to similar parts in the embodiment according to FIGS. 7-10 have been provided with the same reference symbols. The essential difference is the configuration of the widened portion of the tube at the fixing member. As can best be seen from FIG. 11, on the fixing member the porous foam material coatings have been lent a shape which facilitates the fastening of the fixing member to a curved body surface of the patient, for example to a joint.

Figure 13:
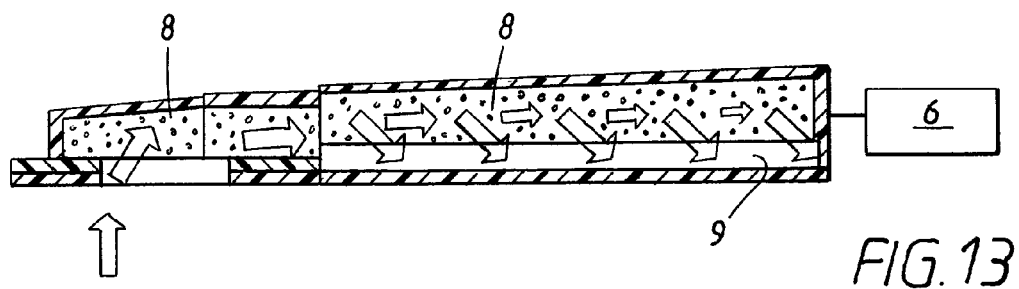
FIG. 13 shows schematically the path of the exudate into a tube according to the present invention.

In FIG. 13 is shown a modified version of a foam material tube forming part of the device according to the invention. In FIG. 13, the path of wound exudate from the wound pocket into the tube serving as a fluid receptacle has been marked with arrows. In the fixing member 4 of the tube, the interior of the tube incorporates only a hydrophobic foam material 8, whilst the tube otherwise has a hydrophobic 8 and a hydrophilic coating 9. As is shown in the drawing, a pump 6 can be connected to the tube serving as a fluid receptacle. The exudate is transported rapidly through the hydrophobic coating 8 and is gradually sucked up by the hydrophilic coating 9. The hydrophilic coating has worse fluid-transporting capacity than the hydrophobic coating, but has the capacity to absorb and retain fluid. The hydrophilic coating has higher fluid affinity than the hydrophobic coating and the fluid absorbed in the hydrophilic coating does not return to the hydrophobic coating. Should the underpressure for some reason cease, the fluid absorbed in the hydrophilic coating is retained. In addition, the hydrophilic coating, as a result of its higher fluid affinity compared with the hydrophobic coating, will continue to absorb fluid from the hydrophobic coating if the underpressure ceases. Apart from the fact that the hydrophilic coating has the capacity to absorb wound fluid, it will also serve as a kind of one-way valve and prevent wound fluid in the hydrophobic coating from being transported back to the wound pocket. This is especially important in wounds on the lower regions of the legs and on the feet of patients, which wound types are common in patients with diabetes. In such wounds, the part serving as a fluid receptacle is situated higher up on the patient when the latter is standing or sitting, and fluid accumulated in a fluid column in a hydrophobic coating exerts a pressure which, without the presence of the hydrophilic coating, could drive wound fluid back to the wound pocket. The absorbency of the absorbent hydrophilic foam material coating can be substantially increased by placing highly absorbent material in this coating, for example particles of CMC. The capacity of highly absorbent particles to swell and suck up fluid from the pores in the hydrophilic coating helps to maintain the underpressure in the tube for a lengthy period, which is essential when a supplementary electric pump does not form part of the device or should an integral pump for some reason cease to function.

An example of a suitable highly absorbent material is a powder with the trade name Oasis 505, which is produced by the company Technical Absorbents.

A tube forming part of the device according to the invention expediently has a hydrophobic coating along the whole of its length for the rapid transport of fluid. By contrast, the hydrophilic coating can be placed along only one portion or along more than one separate portions of the tube.

Figure 14:
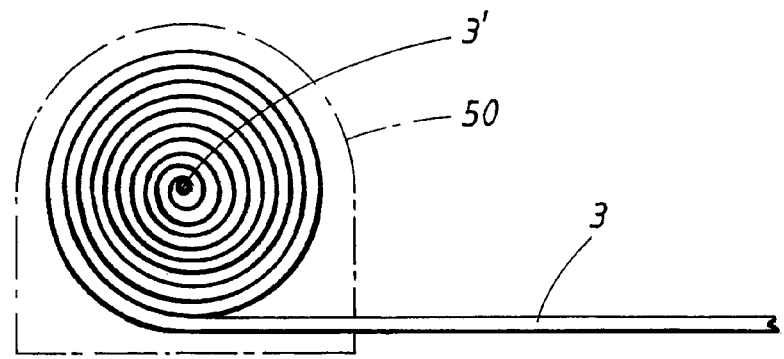
FIG. 14 shows schematically a first illustrative embodiment of a fluid-receiving element forming part of the device according to the invention.
Figure 15:
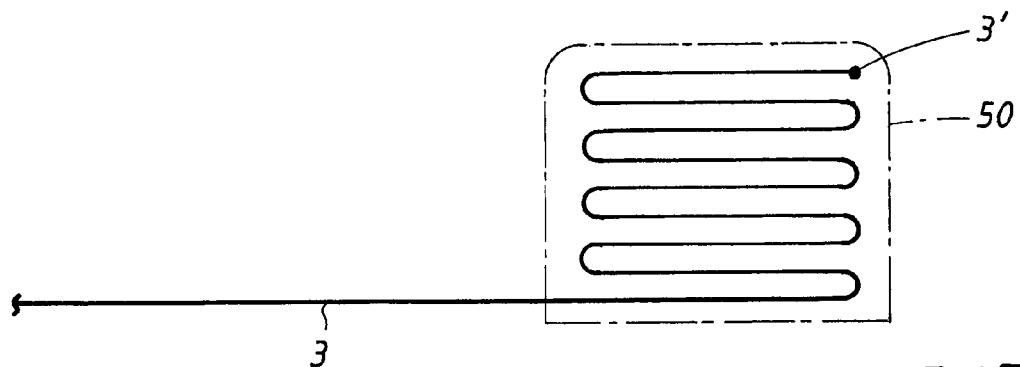
FIG. 15 shows schematically a second illustrative embodiment of a fluid-receiving element forming part of the device according to the invention.

As is shown in FIG. 1, the device can incorporate a separate fluid receptacle to which the tube is connected. In FIGS. 14 and 15, two embodiments are shown in which the fluid receptacle has been formed by rolling-up or folding of a long portion of the tube 3. The end of the tube is provided with a discharge valve 3'. The roll or the folded portion is enclosed in an elastic casing 50. The receptacle formed by the rolled or the folded portion serves also as a pressure source. The receptacle is compressed manually, enclosed air being pumped out through the discharge valve. When the elastically compressible foam material in the tube is subsequently allowed to swell, the receptacle reverts to its original shape and an underpressure is generated in the tube.

The embodiments according to FIGS. 14 and 15 can be arranged such that an arbitrary tube length can be extended according to requirement, i.e. depending on where the wound of the patient and where it is appropriate to place the fluid-receiving receptacle. In the tube, a highly absorbent material which swells upon absorption, such as CMC, can expediently be placed. This material can be placed along the whole of the tube or along one or more portions. Expediently, the concentration of highly absorbent material can be higher towards the end of the rolled or folded tube in the fluid receptacle. By the end of the tube is meant the end where the discharge valve 3' is disposed. Higher concentration of highly absorbent material, so-called super-absorbent material, at the end of the tube can be suitable for facilitating the fluid transport in the tube and for optimal utilization of the absorbency of the tube along the entire length of the tube.

Figure 16:
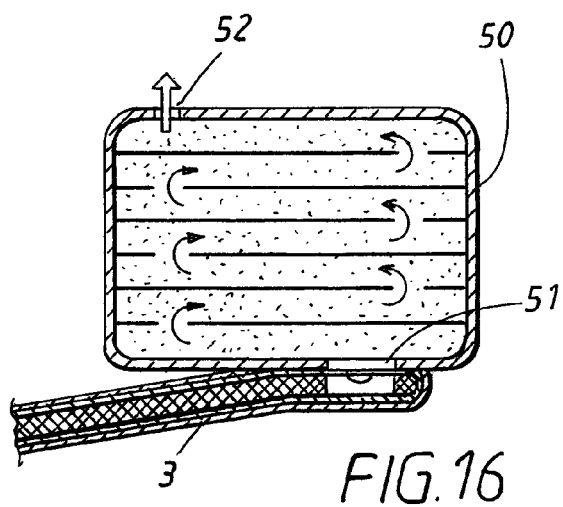
FIG. 16 shows schematically a third illustrative embodiment of a fluid-receiving element forming part of the device according to the invention.

In FIG. 16, a modified version of the fluid receptacle serving as an underpressure source is shown. The tube 3 is connected to the receptacle 5 via an opening 51 in the casing 50 of the receptacle. The fluid-absorbent material in the receptacle is constituted by a number of separate layers of open-pored foam material, in which adjacent layers are separated by intervening plastics films, which are provided with openings for the permeation of fluid from layer to layer in the direction away from the tube 3 towards a discharge valve 52. In FIG. 16, the path of transport of the fluid through the receptacle has been marked with arrows. The layers of foam material in the receptacle, placed one upon another, according to FIG. 16 therefore function essentially like the folded tube shown in FIG. 15. Expediently, each layer has a longitudinal coating of a hydrophobic foam material to allow effective fluid transport through all layers in the direction of the discharge valve, i.e. so that the absorbency of all the layers can be utilized. The said layers also incorporate, at least in a part thereof, a coating of a hydrophilic foam material. The coatings of foam material therefore function essentially like the tube 3 as regards fluid transport and fluid absorption. The layers can also incorporate highly absorbent material. Higher concentration of highly absorbent materials, so-called super-absorbent material, in the layers next to the discharge valve can be suitable for facilitating the fluid transport through the layers and for optimal utilization of the absorbency of all the layers.

Figure 17:
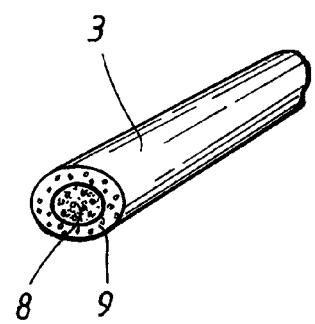
FIG. 17 shows schematically a fourth embodiment of a tube forming part of the device according to the invention.

FIG. 17 shows an alternative version of the tube 3. The tube has an oval or circular cross section comprising a central strand 8 of an open-fibred hydrophobic foam material and an outer coating, of annular cross-section, of an open-pored hydrophilic foam material. The tube according to the figure is provided with a fluid-tight casing, for example in the form of a flexible plastics film.

Figure 6:
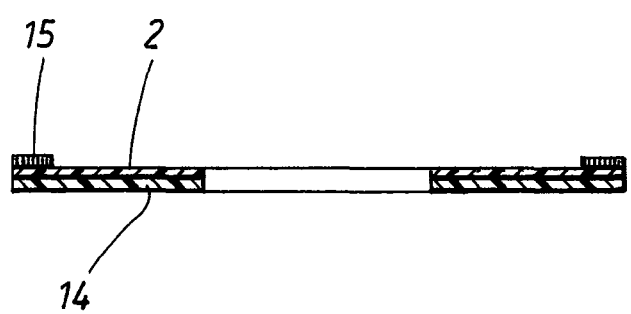
FIG. 6 shows a section along the line VI-VI in FIG. 5.
Figure 7:
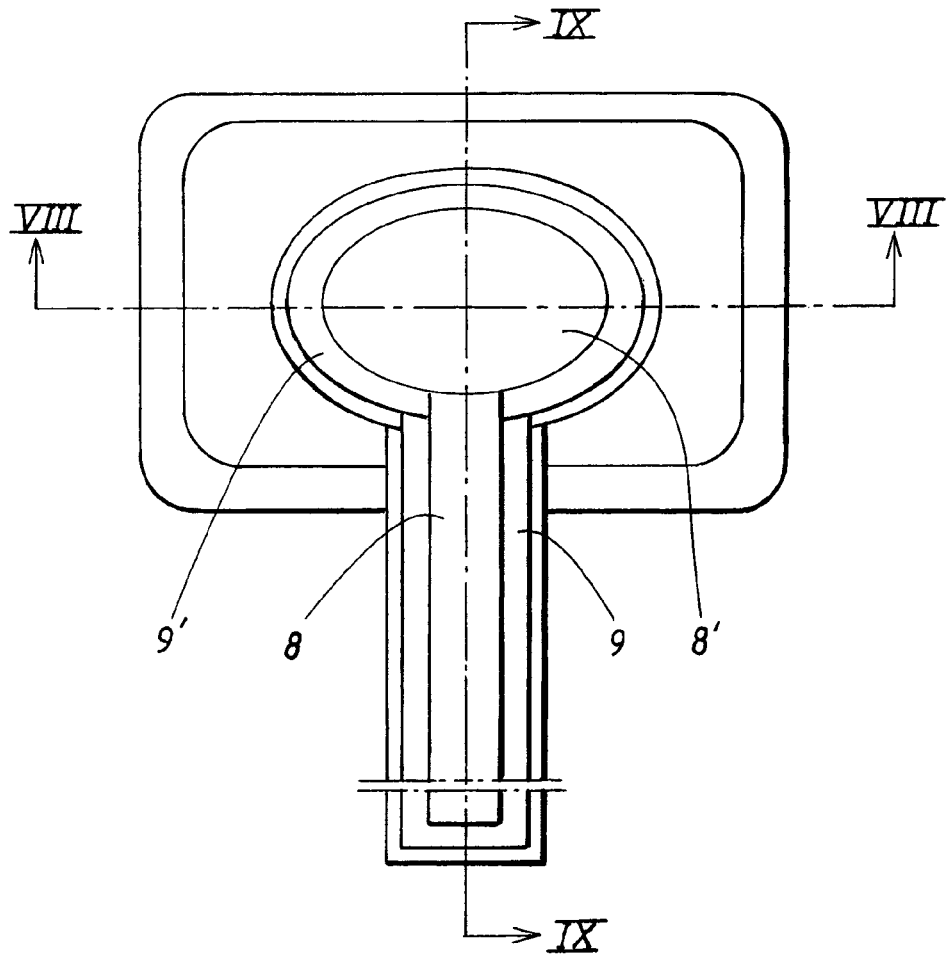
FIG. 7 shows in top view a second embodiment of a tube forming part of the device according to the invention, with associated fixing member.
Figure 18:
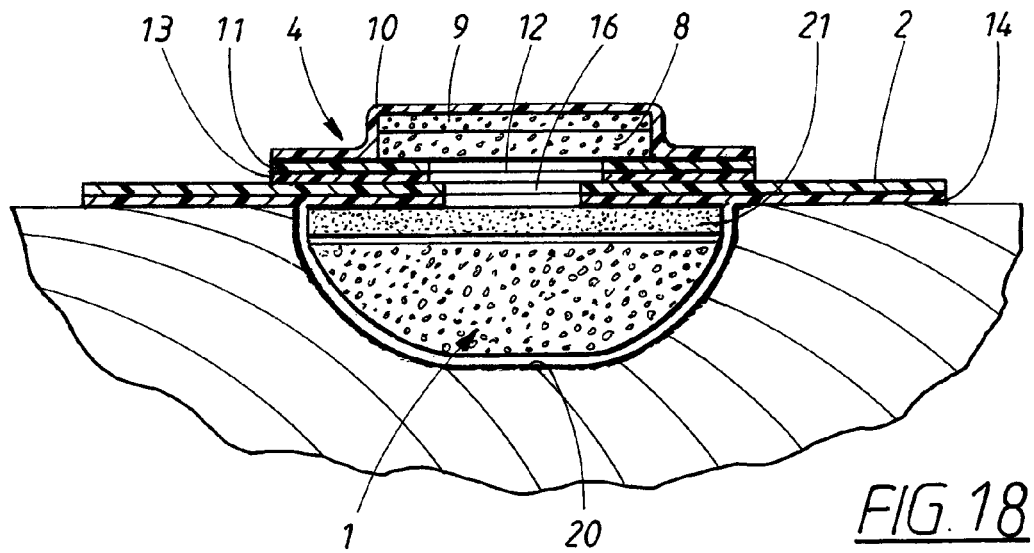
FIG. 18 shows a section through an illustrative embodiment of the device according to the invention in applied position in a wound.

The embodiment shown in FIG. 18 incorporates a material piece 1 placed in a wound pocket 20 and made of a hydrophobic, open-pored foam material, for example a polyurethane foam. This material piece is cut to the shape of the wound. This embodiment further incorporates an absorption body 21 placed in a wound pocket and made of a hydrophilic, open-pored foam material. A sealing film 2 of the kind described in connection with FIGS. 5 and 6 is placed over the wound with the made hole 16 right in front of the wound and by means of a bonding agent 14, expediently of silicone, so as to seal tight against the skin of the patient around the wound. The fixing member 4 of the tube 3 is sealingly placed against the outer side of the sealing film around the made hole. The fixing member 4 and associated tube is of the kind which described above in connection with the embodiment according to FIGS. 2-4. A further positive effect of the underpressure is that the skin lying around the wound also benefits from the underpressure. Oedema, sweat, etc. is sucked along by the underpressure.

A fundamental advantage of the tube forming part of the device according to the invention is that it can be easily connected to the top side of the outer side of the sealing film without protruding parts being formed around the wound site. By virtue of the fact that the fixing surface of the fixing member 4 is smooth and, upon fastening, is applied to the smooth surface of the sealing film 2, as is shown in FIG. 18, a very good connection between the tube and the sealing film is easily obtained, in which risks of gas or fluid leakage have been eliminated. The use of a silicone adhesive further increases the leak-proofness. Examples of a suitable silicone for this purpose. In previously used devices for the vacuum treatment of wounds, fundamental problems have been encountered in connecting conventional tubes to the space in the wound pocket beneath the sealing film. In these previous devices, the tube was first connected to an absorption body in the wound pocket, after which an attempt was made to form a seal by placing the sealing film also over a tube portion. Fastening and sealing around the tube was therefore awkward and time-consuming and great precision was necessary to avoid leakage.

The material piece 1 is intended to virtually fill the wound pocket. It is a significant advantage that the foam material piece 1 is hydrophobic in order that exudate from the wound surface shall not remain on and in the foam material piece, but instead is transported away.

The hydrophilic absorption body 21 is placed on top of the hydrophobic material piece 1 in the wound pocket and beneath the made hole in the sealing form. When underpressure is in force, exudate is transported from the wound via both the hydrophobic material piece 1 and the hydrophilic absorption body to the fluid-receiving element. Should the underpressure for some reason cease, the hydrophilic absorption body serves as a barrier and prevents the transport of previously sucked-up exudate back to the wound. The hydrophilic absorption body therefore serves as a one-way valve. If the underpressure ceases, the hydrophilic absorption body will further continue to suck up fluid from the hydrophobic material piece right until the hydrophilic absorption body is saturated with fluid.

In the hydrophobic material piece and/or in the hydrophilic absorption body can be placed active carbon for the elimination of foul-smelling odours which can be generated in some wounds. Alternatively, active carbon can be placed in the tube and/or the receptacle for the collection of wound fluid.

Figure 19:
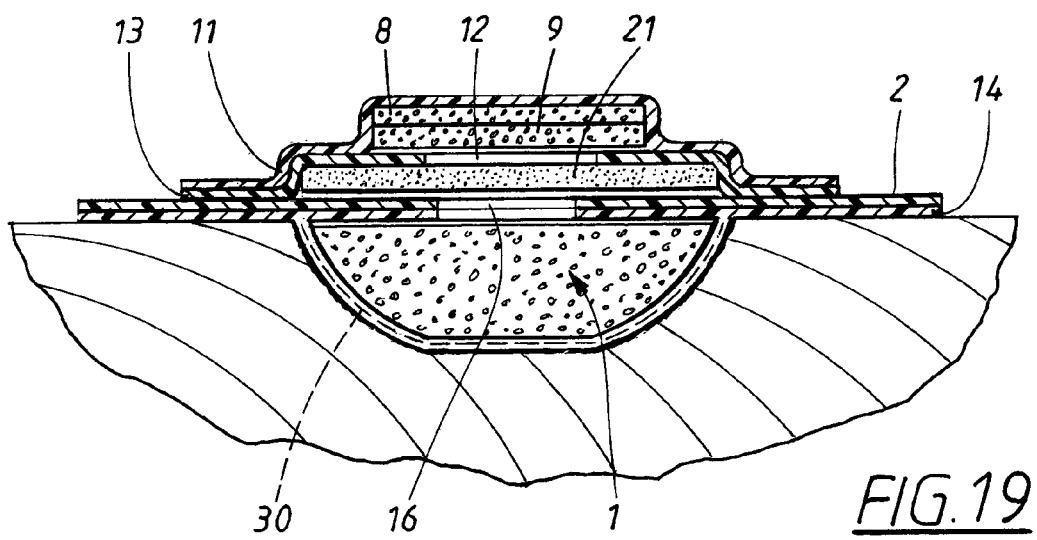
FIG. 19 shows a section, corresponding to that in FIG. 18, according to a somewhat modified embodiment.

The embodiment shown in FIG. 19 functions broadly like the embodiment according to FIG. 18 as regards the absorption and transport of fluid. One difference is that that the hydrophilic absorption body 21 has been placed on top of the sealing film right in front of the hole 16 made therein. In the embodiment according to FIG. 19, the absorption body 21 forms an effective one-way valve and will also suck fluid from the hydrophobic material piece 1 within the sealing film should the underpressure for some reason cease. As can be seen from FIGS. 18 and 19, the hydrophobic coating 8 and the hydrophilic coating 9 have been able to change place in the tube. This has been done to indicate that for the working of the tube it is not critical which of the coatings is situated next to the patient when the tube is used.

This applies, of course, to other shown embodiments of the tube. If the hydrophilic coating is wished to serve as a one-way valve to prevent fluid from flowing back to the wound pocket should the underpressure for some reason cease, it is of course a significant advantage that the tube portion, at least right in front of the opening in the sealing film, has the hydrophilic coating next to the patient.

In the embodiment shown in FIG. 19, an elastic mesh 30, which is encapsulated in a soft and elastic hydrophobic gel, for example a silicone gel, is placed directly against the wound. The hydrophobic gel encapsulates the wires in the meshwork and the mesh as a whole has through-openings formed by the meshwork. A suitable example of an elastic mesh 30 is described in EP 0 261 167 B1. In this publication, an example is also given of a suitable silicone gel for this purpose, namely a gel which is marketed by Dow Corning under the brand name Dow Corning Q7-2218.

Figure 20:
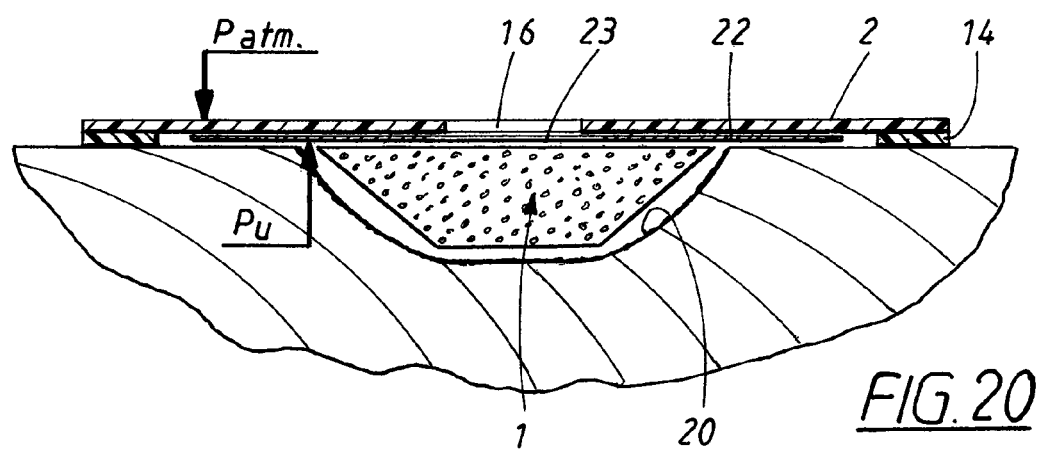
FIG. 20 shows a section, corresponding to that in FIGS. 18 and 19, through a further illustrative embodiment and prior to the fitting of the tube.

The embodiment shown in FIG. 20 incorporates a thin and soft hydrophobic plastics film 22, which is provided with a central hole 23. The plastics film 22 is placed covering the wound pocket and covering a portion of skin around the wound pocket. The hydrophobic thin and soft film protects the edges of the wound and provides increased security against gas leakage to and from the wound pocket. The atmospheric pressure $P_{atm}$ is higher than the underpressure $P_u$ in the wound pocket and will be sucked tight against the skin surrounding the wound and provide good sealing should the binding agent 14 on the sealing film 2 for some reason not be fully gas-tight.

Alternatively, the plastics film 22 can be replaced by a thin, soft hydrophobic sheet of some other material, such as non-woven fabric or foam.

Figure 21:
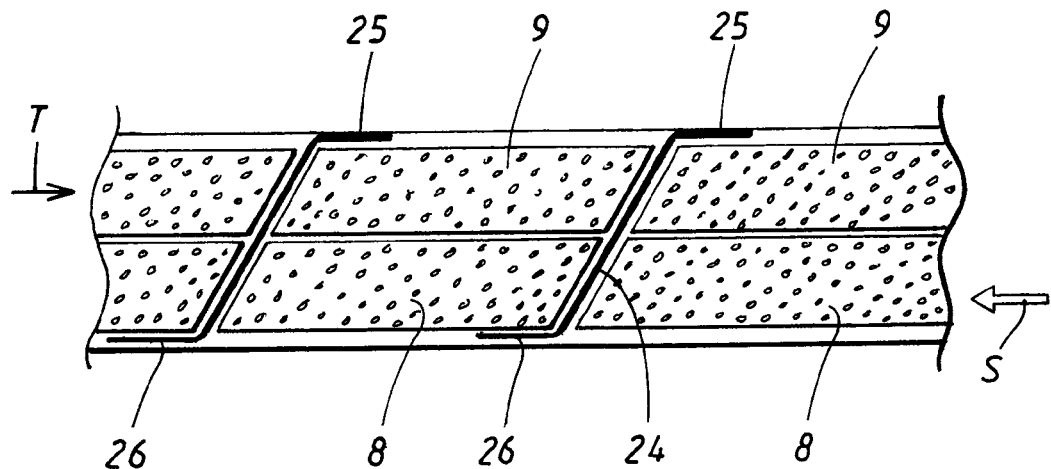
FIG. 21 shows a cross section through a fifth embodiment of a tube forming part of the device according to the invention.

In the embodiment of the tube 3 which is shown in FIG. 21, it is shown schematically how one-way valves in the form of diaphragm valves 24 made of flexible plastics film have been fitted in the interior of the tube. The said plastics films are connected to the casing of the tube along portions 25, whilst portions 26 are freely movable in relation to the casing. Fluid is therefore allowed to flow only in the direction of the arrow S, transport being realized beneath the unbonded portions 26 of the plastics film. By contrast, fluid flow in the direction of the arrow T is prevented by the diaphragm valves, since the portions 26 are pressed sealingly against the tube casing when the flow is in this direction.

Figure 22:
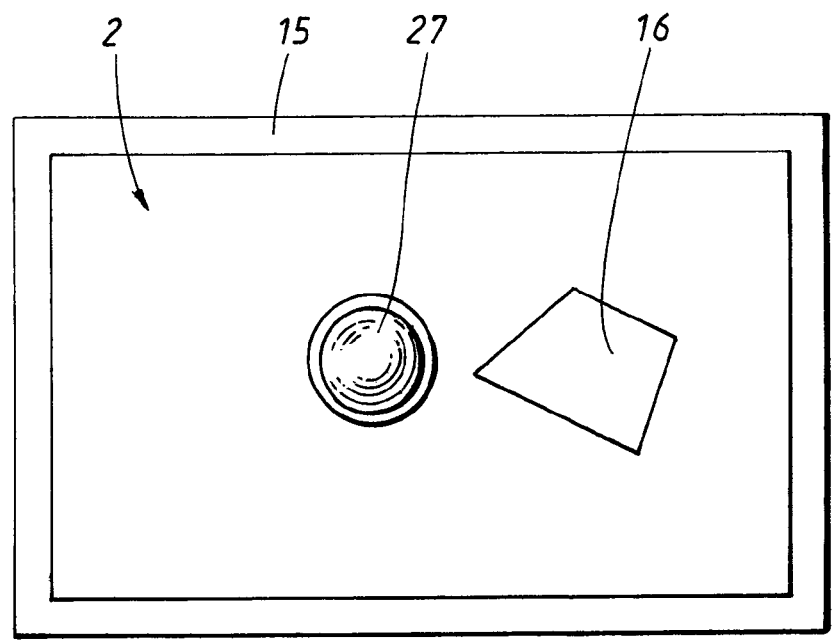
FIG. 22 shows a sealing film having a penetration member attached to the outer side thereof.

In FIG. 22 is shown an embodiment in which the device according to the invention has been supplemented by a penetration member 27. This is connected with a bonding agent to the sealing film above the wound pocket. The penetration member is expediently separate and is fixed to the sealing film when there is a need for the addition of rinsing fluid for cleansing of the wound or for the addition of a wound-healing stimulant. The penetration member is constituted by a material coating penetrable with a cannula, which material is self-sealing when the cannula is extracted.

The device according to the invention is not limited to the above-described embodiments, but rather a number of variants are possible within the scope of the following patent claims.

For example, in the embodiment according to FIG. 19, the mesh 30 can be replaced by a coating of an elastic hydrophobic gel, such as a silicone gel. In connection with the application to the hydrophobic foam material, this coating can be made to penetrate a bit into the pores of the foam material to form flow holes for wound fluid into the pores of the foam material. A foam material having such a coating is described in EP 0 855 921 B1.

Alternatively, the foam material can be coated with a layer of a hydrophobic gel, which, after the coating, is perforated to form flow ducts for wound fluid.

In the above-described illustrative embodiments, open-pored foam material has been specified as the hydrophilic and hydrophobic material strands. Other hydrophilic and hydrophobic materials are, of course, conceivable within the scope of the following patent claims. The crux is that the material strands are soft and elastic.

For example, fibres of different kinds, such as cellulose fibres, textile fibres and thermoplastic fibres, or mixtures thereof, can be used to produce hydrophilic or hydrophobic material strands having characteristics suitable for the purpose, i.e. suitable fluid-transporting capacity for the hydrophobic material strand and suitable fluid-holding capacity of the hydrophilic strand when there is underpressure in the tube or at atmospheric pressure.

The cross-section of the tube 3 does not need to be configured as in the above-described illustrative embodiments, but rather a number of variants are conceivable. For example, a number of hydrophilic material strands and a number of hydrophobic material strands can be incorporated. The tube can also be formed by a hydrophobic sheet and a hydrophilic sheet placed on top of this, which sheets have been rolled into a roll having a multilayered structure of hydrophilic and hydrophobic coatings.

The invention also comprises embodiments in which the above-described soft tube merges into a conventional silicone tube before it is coupled to the collecting receptacle, for example at a valve coupled to the collecting receptacle. In this region, patient comfort is obviously not as critical with regard to chafing hard tubes.

The invention claimed is:

1. A device for treating wounds with reduced pressure, the device comprising:
   a sealing film configured to be placed sealingly around the wound and cover the wound;
   an underpressure source; and
   a tube, wherein the tube is configured to connect a space over the wound and beneath the sealing film to the underpressure source, wherein the interior of the tube comprises at least one longitudinal first strand made of a hydrophobic, soft and elastic material, wherein the interior of the tube over at least a part of its length has at least one longitudinal second strand separate from said first strand and made of a hydrophilic material, and wherein the tube comprises a casing made of a flexible material configured to enclose the longitudinal first and second strands.

2. The device of claim 1, wherein the longitudinal first strand is comprised of a hydrophobic, open-pored foam material, and wherein the longitudinal second strand is comprised of a hydrophilic, open-pored foam material.

3. The device of claim 1, wherein the longitudinal first and second strands are placed one over the other and wherein each of the longitudinal first and second strands has a rectangular cross section.

4. The device of claim 1, wherein the underpressure source is configured to serve as a fluid-receiving element for fluid aspirated from the wound, and wherein the underpressure source comprises an elastically resilient, open-pored foam material, and a one-way valve, the one-way valve being arranged to allow an outflow of air from the underpressure source when the underpressure source is compressed.

5. The device of claim 4, wherein the fluid-receiving element is comprised of a folded or rolled-up portion of the tube.

6. The device of claim 4, wherein at least one of the tube and the fluid-receiving element comprises a super-absorbent material.

7. The device of claim 4, further comprising a manual pump, wherein the manual pump is configured for detachable connection to the fluid-receiving element.

8. The device of claim 4, wherein active carbon is placed in the fluid-receiving element.

9. The device of claim 1, wherein one end portion of the tube casing comprises a fixing member for fastening the end portion onto the outer side of the sealing film right in front of a hole made therein, which hole, when the device is used, is placed above the space over the wound, and wherein the end portion has an opening for connection to the hole.

10. The device of claim 9, wherein the fixing member comprises a tab made of a plastics film, which tab comprises a peripherally placed fixing means configured for sealing connection to the outer side of the sealing film around the hole.

11. The device of claim 10, further comprising an absorption body made of a hydrophilic, porous material, and wherein the absorption body is adapted to be placed over the hole in the sealing film between the sealing film and the plastics tab.

12. The device of claim 11, wherein the hydrophilic, porous material comprises an open-pored foam material.

13. The device of claim 1, further comprising a hydrophobic, porous material piece wherein the material piece can be configured in the shape of the wound and adapted to be placed in the wound beneath the sealing film.

14. The device of claim 13, wherein active carbon is placed in the porous material piece.

15. The device of claim 13, further comprising an absorption body made of a hydrophilic, porous material wherein the absorption body can be configured in the shape of the wound and adapted to be placed in between the sealing film and the hydrophobic, porous material piece.

16. The device of claim 15, wherein the hydrophilic, porous material comprises an open-pored foam material.

17. The device of claim 13, wherein the hydrophobic, porous material piece, on a side thereof that is placed against the wound surface during use, is coated with a perforated coating of an elastic, hydrophobic gel.

18. The device of claim 17, wherein the elastic, hydrophobic gel comprise silicone gel.

19. The device of claim 13, wherein the hydrophobic, porous material piece comprises an open-pored foam material.

20. The device of claim 1, further comprising an electric pump.

21. The device of claim 20, wherein the pump comprises a battery-powered piezoelectric pump.

22. The device of claim 20, wherein the pump is configured for detachable connection to the underpressure source.

23. The device of claim 1, further comprising a manual pump.

24. The device of claim 1, further comprising a separate opening diaphragm, wherein the diaphragm is provided with fixing means for fastening onto the outer side of the sealing film, wherein the diaphragm is configured to be fixed to the sealing film over the wound, wherein the diaphragm comprises a material penetrable with a cannula, and wherein the material is self-sealing following removal of the cannula.

25. The device of claim 1, further comprising a thin, hydrophobic sheet having a central opening wherein the sheet is configured to be placed over and around the wound beneath the sealing film, wherein the sheet is soft and flexible and is configured to be pressed by the atmospheric pressure into sealing contact with the skin of the patient around the wound.

26. The device of claim 25, wherein the thin hydrophobic sheet is made of non-woven fabric, plastic, or foam material.

27. The device of claim 1, wherein the interior of the tube has at least one diaphragm valve, wherein the at least one diaphragm valve is configured to only allow a flow in the direction away from the wound towards the underpressure source.

28. The device of claim 1, further comprising an elastic mesh, which is coated with a soft, elastic, hydrophobic gel, wherein the mesh is configured to be cut to the size of the wound and adapted to be placed next to the wound surface.

29. The device of claim 28, wherein the soft, elastic, hydrophobic gel comprises silicone gel.

30. The device of claim 1, wherein the sealing film and the tube are formed into an integrated prefabricated unit.

31. The device of claim 1, wherein the tube is connected to the underpressure source by a silicone tube.

* * * * *

UNITED STATES PATENT AND TRADEMARK OFFICE
CERTIFICATE OF CORRECTION

PATENT NO. : 8,545,466 B2  Page 1 of 1
APPLICATION NO. : 12/666002
DATED : October 1, 2013
INVENTOR(S) : Andresen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 804 days.

Signed and Sealed this
Fifteenth Day of September, 2015

Michelle K. Lee
*Director of the United States Patent and Trademark Office*